United States Patent [19]

Schneider

[11] 4,119,648
[45] Oct. 10, 1978

[54] THROMBOXANE B ALDEHYDE INTERMEDIATES

[75] Inventor: William P. Schneider, Kalamazoo Township, Kalamazoo County, Mich.

[73] Assignee: The Upjohn Company, Kalamazoo, Mich.

[21] Appl. No.: 830,520

[22] Filed: Sep. 6, 1977

Related U.S. Application Data

[60] Division of Ser. No. 716,473, Aug. 20, 1976, Pat. No. 4,070,384, which is a continuation-in-part of Ser. No. 676,894, Apr. 14, 1976, Pat. No. 4,018,804.

[51] Int. Cl.$^2$ ............................ C09F 7/02; C11C 3/00
[52] U.S. Cl. ...................................... 260/405; 560/53; 560/177; 424/284; 424/308; 424/312; 260/345.7 P; 424/314

[58] Field of Search ..................... 260/405, 405.5, 406, 260/408, 410, 410.5, 410.9 R; 424/284, 308, 312, 314; 560/53, 177

[56] References Cited

PUBLICATIONS

Samuelsson, B. Proc. Nat. Acad. Sci. U.S.A. 71, pp. 3400–3404 (1974).
K. Heusler et a. Angew Chem. vol. 3 pp. 525–596 (1964).

Primary Examiner—Winston A. Douglas
Assistant Examiner—John F. Niebling
Attorney, Agent, or Firm—Robert A. Armitage

[57] ABSTRACT

The present specification provides novel intermediates and novel processes for the synthesis of various side chain and skeletal analogs of Thromboxane B$_2$ (11$\beta$-homo-11$\alpha$-oxa-PGF$_a$). These analogs are particularly and especially useful as reproductive cycle control agents.

1 Claim, No Drawings

THROMBOXANE B ALDEHYDE INTERMEDIATES

CROSS REFERENCE TO RELATED APPLICATION

The present application is a divisional application of Ser. No. 716,473, filed Aug. 20, 1976, now U.S. Pat. No. 4,070,384; which is a continuation-in-part of Ser. No. 676,894, filed Apr. 14, 1976, issued as U.S. Pat. No. 4,018,804 on Apr. 19, 1977.

The present invention relates to processes and intermediates for Thromboxane B compounds for which the essential material constituting disclosure therefor is incorporated by reference here from U.S. Pat. No. 4,020,173, issued Apr. 26, 1977 and Ser. No. 716,473, filed Aug. 20, 1976, now U.S. Pat. No. 4,070,384.

I claim:

1. A thromboxane intermediate of the formula:

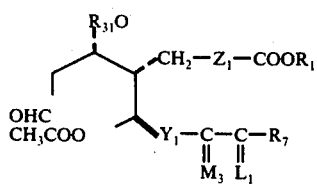

wherein $R_{31}$ is a hydroxy hydrogen replacing group; wherein $Z_1$ is
 (1) cis—CH=CH—CH$_2$—(CH$_2$)$_g$—CH$_2$—,
 (2) cis—CH=CH—CH$_2$—(CH$_2$)$_g$—CH$_2$—,
 (3) cis—CH$_2$—CH=CH—(CH$_2$)$_g$—CH$_2$—,
 (4) —(CH$_2$)$_3$—(CH$_2$)$_g$—CH$_2$—,
 (5) —(CH$_2$)$_3$—(CH$_2$)$_g$—CF$_2$—,
 (6) —CH$_2$—O—CH$_2$—(CH$_2$)$_g$—CH$_2$—,

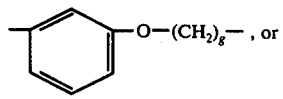 (7)

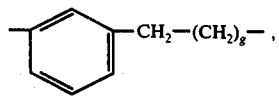 (8)

wherein $g$ is one, 2, or 3;
 wherein $R_1$ is alkyl of one to 12 carbon atoms, inclusive, cycloalkyl of 3 to 10 carbon atoms, inclusive, aralkyl of 7 to 12 carbon atoms, inclusive, phenyl, phenyl substituted with one or two chloro, fluoro, or alkyl of one to 4 carbon atoms, inclusive, or a pharmacologically acceptable cation;
 wherein $Y_1$ is trans—CH=CH— or —CH$_2$CH$_2$—;
 wherein $M_3$ is .

or

wherein $R_5$ is hydrogen or methyl and $R_{31}$ is a hydroxy-hydrogen replacing group;
 wherein $L_1$ is

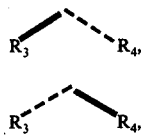

or a mixture of

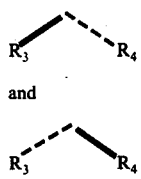

and

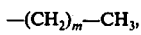

wherein $R_3$ and $R_4$ are hydrogen, methyl, or fluoro, being the same or different with the proviso that one of $R_3$ and $R_4$ is methyl only when the other is hydrogen or methyl; and
 wherein $R_7$ is —(CH$_2$)$_m$—CH$_3$, (1)

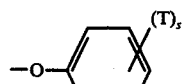 (2)

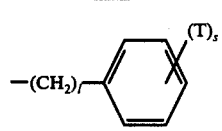 (3)

wherein $l$ is zero, one, two, or three, wherein $m$ is one to 5, inclusive, T is alkyl of one to 3 carbon atoms, inclusive, alkoxy of one to 3 carbon atoms, inclusive, chloro, fluoro, or trifluoromethyl, and $s$ is one, two, or 3, the various T's being the same or different, with the proviso that not more than two T's are other than alkyl, with the further proviso that $R_7$ is

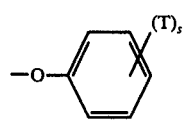

only when $R_3$ and $R_4$ are hydrogen or methyl, being the same or different.

* * * * *

UNITED STATES PATENT OFFICE
CERTIFICATE OF CORRECTION

Patent No. 4,119,648   Dated October 10, 1978

Inventor(s) William P. Schneider

It is certified that error appears in the above-identified patent and that said Letters Patent are hereby corrected as shown below:

Column 1, line 33, "(2) cis-$CH=CH-CH_2-(CH_2)_g-CH_2$,"

should read -- (2) cis-$CH=CH-CH_2-(CH_2)_g-CF_2$, --

Signed and Sealed this

*Thirteenth* Day of *March 1979*

[SEAL]

*Attest:*

RUTH C. MASON
*Attesting Officer*

DONALD W. BANNER
*Commissioner of Patents and Trademarks*